US009678023B2

(12) United States Patent
Kim et al.

(10) Patent No.: US 9,678,023 B2
(45) Date of Patent: Jun. 13, 2017

(54) METHOD OF DETERMINING SURFACE ORIENTATION OF SINGLE CRYSTAL WAFER

(71) Applicant: KOREA RESEARCH INSTITUTE OF STANDARDS AND SCIENCE, Daejeon (KR)

(72) Inventors: Chang Soo Kim, Seongnam-si (KR); Seok Min Bin, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 14/443,026

(22) PCT Filed: May 31, 2013

(86) PCT No.: PCT/KR2013/004828
§ 371 (c)(1),
(2) Date: May 14, 2015

(87) PCT Pub. No.: WO2014/077480
PCT Pub. Date: May 22, 2014

(65) Prior Publication Data
US 2015/0330918 A1 Nov. 19, 2015

(30) Foreign Application Priority Data
Nov. 16, 2012 (KR) .................. 10-2012-0130433

(51) Int. Cl.
*G01N 23/207* (2006.01)
*H01L 21/66* (2006.01)
(52) U.S. Cl.
CPC .......... *G01N 23/207* (2013.01); *H01L 22/12* (2013.01); *G01N 2223/331* (2013.01); *G01N 2223/6116* (2013.01)

(58) Field of Classification Search
CPC ..... G01N 2223/331; G01N 2223/6116; G01N 23/207; H01L 22/12
See application file for complete search history.

(56) References Cited

U.S. PATENT DOCUMENTS 6,376,267 B1   4/2002 Noack et al.
6,873,681 B2 * 3/2005 Toraya ................ G01N 23/207
                                                              378/71

(Continued)

FOREIGN PATENT DOCUMENTS

CN       1529647 A    9/2004
CN     101211866 A    7/2008

(Continued)

OTHER PUBLICATIONS

Doucette, L.D., et al., "Precise orientation of single crystals by a simple x-ray diffraction rocking curve method" Rev. Sci. Instrum. 76, 036106 (2005).*

(Continued)

*Primary Examiner* — Wyatt Stoffa
(74) *Attorney, Agent, or Firm* — McCoy Russell LLP

(57) ABSTRACT

Provided is a method of determining a surface orientation of a single crystal wafer. The method of determining a surface orientation of a single crystal wafer using high resolution X-ray rocking curve measurement may determine a surface angle of the wafer and a direction of the surface angle using rocking curve measurement of a high resolution X-ray diffraction method and measuring a misalignment angle formed by a rotation axis of a measuring apparatus and a surface normal of the wafer and an orientation of the misalignment angle.

5 Claims, 7 Drawing Sheets

(56) References Cited

U.S. PATENT DOCUMENTS

| | | | |
|---|---|---|---|
| 2003/0123610 A1* | 7/2003 | Okanda | G01N 23/20 378/71 |
| 2003/0235270 A1* | 12/2003 | Toraya | G01N 23/207 378/73 |
| 2006/0062351 A1* | 3/2006 | Yokhin | G01N 23/20008 378/86 |
| 2006/0176342 A1 | 8/2006 | Aoto et al. | |
| 2012/0140889 A1* | 6/2012 | Wall | G01N 23/207 378/73 |
| 2012/0140890 A1* | 6/2012 | Ozawa | G01N 23/207 378/74 |
| 2013/0108022 A1* | 5/2013 | Kugland | G21K 1/06 378/84 |
| 2015/0204804 A1* | 7/2015 | Kim | G01N 23/2073 250/391 |

FOREIGN PATENT DOCUMENTS

| | | |
|---|---|---|
| CN | 101680115 A | 3/2010 |
| JP | S5320354 A | 2/1978 |
| JP | S57136151 A | 8/1982 |
| JP | S59225339 A | 12/1984 |
| JP | H0319250 A | 1/1991 |
| JP | 10144772 A | 5/1998 |
| JP | H10253553 A | 9/1998 |
| JP | H1137958 A | 2/1999 |
| JP | H1164252 A | 3/1999 |
| JP | 2002139463 A | 5/2002 |
| JP | 2011003929 A | 1/2011 |

OTHER PUBLICATIONS

ASTM F26-87a (1999), "Standard Test Methods for Determining the Orientation of a Semiconductive Single Crystal" (Withdrawn 2003), ASTM International, West Conshohocken, PA, 1999, 5 pages.

ISA Korean Intellectual Property Office, International Search Report Issued in Application No. PCT/KR2013/004828, Oct. 16, 2013, WIPO, 3 pages.

* cited by examiner

METHOD OF DETERMINING SURFACE ORIENTATION OF SINGLE CRYSTAL WAFER

CROSS REFERENCE TO RELATED APPLICATIONS

The present application is a U.S. National Phase of International Patent Application Serial No. PCT/KR2013/004828, entitled "METHOD OF DETERMINING SURFACE ORIENTATION OF SINGLE CRYSTAL WAFER," filed on May 31, 2013, which claims priority to Korean Patent Application No. 10-2012-0130433, entitled "METHOD OF DETERMINING SURFACE ORIENTATION OF SINGLE CRYSTAL WAFER," filed on Nov. 16, 2012, the entire contents of each of which are hereby incorporated by reference for all purposes.

TECHNICAL FIELD

The present invention relates to a method of determining a surface orientation of a single crystal wafer, and more particularly, to a method of determining a surface orientation of a single crystal wafer using high resolution X-ray rocking curve measurement capable of determining a surface angle of the wafer and a direction of the surface angle using rocking curve measurement of a high resolution X-ray diffraction method and measuring a misalignment angle formed by a rotation axis of a measuring apparatus and a surface normal of the wafer and an orientation of the misalignment angle.

BACKGROUND ART

A single crystal wafer of silicon, sapphire, gallium arsenide, or the like, for manufacturing a semiconductor device is manufactured so as to have a predetermined crystallographical directional property. In the case of the single crystal wafer, since general information on a surface orientation of the wafer is present and a single crystal is well processed, an axis orientation of the wafer may be determined using an X-ray.

A general single crystal wafer has been produced according to standards such as an angle between a surface and a crystal plane of 0±0.5° and 4±0.5°, a horizontal component of a surface orientation of 0.2±0.05°, and a vertical component of a surface orientation of 0±0.1° with respect to a (100) wafer or a (111) wafer. As a usual single crystal wafer usually used as a material of a semiconductor device, a wafer of which a surface normal is tilted with respect to a silicon crystal plane normal by about 0 to 4° is used. Since this angle (a surface orientation, off-cut angle, surface miscut, or surface misorientation) and a direction (an off-cut or miscut direction) in which the surface normal of the wafer is tilted have an effect on a physical property of a manufactured semiconductor device, it is very important to accurately measure the surface orientation. In addition, since this angle and this direction are important factors in determining productivity of the device, they have been importantly controlled in a production line of the wafer for a semiconductor device.

For these reasons, accuracy of an apparatus of measuring and inspecting the surface orientation becomes a decisive factor in determining quality of a product as well as productivity of the production line. Therefore, the apparatus of measuring the surface orientation of the wafer needs to be accurately calibrated before subsequent processing processes such as a polishing process, and the like.

In order to accurately determine an accurate angle formed by the surface normal of the wafer and a vertical axis of the crystal plane and a direction of the angle, a measuring method using an X-ray diffractometer (hereinafter, referred to as an XRD) has been demanded.

Meanwhile, a standard for measuring a crystallographical surface orientation of a single crystal wafer using the XRD has been defined in a standard procedure ASTM F26-87a (Standard Test Method for Determining the Orientation of a Semiconductive Single Crystal). In the ASTM F26-87a standard, which is a standard for measuring a crystallographical orientation of a semiconductive single crystal, a method using an XRD and an optical method have been described. In the method using an XRD, procedures such as an X-ray diffraction theory for measuring an orientation of a semiconductive single crystal, a measuring apparatus, a measuring method, an analyzing method, and the like, has been described.

However, this standard has been described under the assumption that a surface normal of a wafer is the same as a rotation axis of a measuring apparatus. In a general case, since the surface normal of the wafer does not coincide with the rotation axis of the measuring apparatus, a measuring error corresponding to an angle at which they do not coincide with each other is caused. Therefore, in the case in which the surface normal of the single crystal wafer requiring a precise surface orientation is significantly different from the rotation axis of the measuring apparatus, large uncertainty is caused in measuring the surface orientation of the wafer.

DISCLOSURE

Technical Problem

An object of the present invention is to provide a method of determining a surface orientation of a single crystal wafer capable of precisely determining not only the surface orientation, that is, a surface angle, of the single crystal wafer but also a direction of the surface angle using rocking curve measurement of a high resolution X-ray diffraction method.

Particularly, an object of the present invention is to provide a method capable of accurately determining a surface orientation of a wafer in consideration of misalignment between a rotation axis of an apparatus of measuring a surface orientation and a surface normal of the wafer without arranging the rotation axis and the surface normal using a surface orientation standard material even in the case in which the rotation axis and the surface normal do not coincide with each other and is to provide a method of determining a surface orientation of a single crystal wafer using high resolution X-ray rocking curve measurement capable of measuring an angle formed by a surface normal of the wafer and a rotation axis of a measuring apparatus and a direction of the angle.

Technical Solution

In one general aspect, there is provided a method of measuring a surface orientation of a signal crystal wafer in order to determine the surface orientation formed by a crystal plane normal of a single crystal and a surface normal of the wafer, wherein the wafer is rotated by a predetermined rotation angle (θ) with respect to the surface normal thereof to measure a high-resolution X-ray rocking curve of a selected diffraction plane under an optimal Bragg diffraction condition, and a position ($\omega_\phi$) of a maximum peak of the high-resolution X-ray rocking curve is determined by the following Equation:

$$\omega_\phi = \omega_0 + \Delta\omega\phi = \theta_E + \delta_0 - \delta_{P(R)}$$

where $\omega_0$ indicates an incident angle of an X-ray, $\theta_E$ indicates a Bragg angle, $\delta_0$ indicates a misalignment angle formed by a rotation axis and the surface normal, and $\delta_{P(R)}$ indicates an angle between a rotation axis of a measuring apparatus and a surface normal on a diffraction plane rotated by A tilt angle ($\delta S(R)$) of the surface normal of the wafer may be determined by the following Equation:

$$\delta_{S(R)} \cong \delta_0 \cdot \cos(\phi - \phi_\phi) - \delta_{S(R)}$$

where $\delta_\phi$ indicates a phase of the surface normal, and $\delta_{S(R)}$ indicates a geometrical small angle component.

At the rotation angle $\phi=0$ the position ($\omega_\phi$) of the maximum peak of the high-resolution X-ray rocking curve may be determined by the following Equation:

$$\omega_\phi \cong \theta_B + \delta_0 \cdot \cos(-\phi_\phi) - \kappa_{S(R)(\phi=0)} - \delta_{P(R)}$$

where $\phi_\phi$ indicates a phase of the surface normal, and $\kappa_{S(R)}$ indicates a geometrical small angle component.

An angle ($\delta_{P(R)}$) between the rotation axis and the crystal plane normal having a function on the diffraction plane may be determined by the following Equation:

$$\delta_{P(R)} \cong \delta_1 \cdot \cos(\phi - \phi_\phi) + \delta_0 \cdot \cos(\phi - \phi_\phi) - \kappa_{P(R)}$$

where $\delta_1 \cdot \cos(\phi - \phi_\phi)$ indicates an angle component of the crystal plane normal changed along a circumference of the surface normal, and $\delta_0 \cdot \cos(\phi - \phi_\phi)$ indicates an angle component of the surface normal changed along a circumference of the rotation axis.

When considering misalignment of the rotation axis rotating the wafer, the position ($\omega_\phi$) of the maximum peak of the high-resolution X-ray rocking curve may be determined by the following Equation:

$$\omega_\phi \cong -\delta_1 \cdot \cos(\phi - \phi_\phi) - \delta_0 \cdot \cos(\phi - \phi_\phi) + \kappa_{P(R)} + \theta_B + \delta_0 \cdot \cos(-\phi_\phi) - \kappa_{S(R)(\phi=0)}$$

where $\delta_1$ indicates an angle (surface angle) of the crystal plane normal with respect to the surface normal, $\phi_\phi$ indicates a direction in which the surface angle appears, $\delta_0$ indicates a misalignment angle formed by the rotation axis and the surface normal, $\phi_\phi$ indicates a direction of a misalignment axis, $\kappa_{P(R)}$ indicates a small angle component, $\theta_B$ indicates a Bragg angle, and the remainings indicate constants.

The surface angle ($\delta_1$) of the wafer and the direction ($\phi_\phi$) in which the surface angle appears may be determined by the following Equation:

$$\omega_\phi - \omega'_\phi \cong 2\delta_1 \cdot \sin\frac{\Delta\phi_p}{2} \cdot \sin\left(\phi - \phi_p - \frac{\Delta\phi_p}{2}\right)$$

where $\Delta\phi_\phi$ indicates a phase change value applied at the time of designing a wafer holder, and $\omega_\phi - \omega'_\phi$ indicates an angle difference between peaks of the high-resolution X-ray rocking curve each measured depending on $\Delta\phi_\phi$, and a variation ($\delta_{P(S)}$) of the surface orientation of the wafer depending on a function of the orientation angle ($\theta$) may be determined by the following Equation:

$$\delta_{P(S)} \cong \delta_1 \cdot \cos(\phi - \phi_\phi).$$

The high-resolution X-ray rocking curve may be measured two times at $\phi = \phi_1$ and $\phi = \phi_2$, and $\Delta\phi_\phi$ may be determined by the following Equation: $\Delta\phi_\phi = \phi_2 - \phi_1$.

A tilt variation ($\delta_{S(R)}$) of the surface normal from the rotation axis depending on the function of the orientation angle ($\delta$) may be determined by the following Equation:

$$\delta_{S(R)} \cong \delta_0 \cdot \cos(\phi - \phi_\phi)$$

where $\delta_0$ indicates the misalignment angle formed by the rotation axis and the surface normal, and $\phi_\phi$ indicates the direction of the misalignment axis.

An angle component ($\delta_1 \cdot \cos \phi_\phi$) of the surface orientation of the wafer along a direction of 0 to 180° may be determined by the following Equation:

$$\delta_1 \cdot \cos \phi_\phi = \frac{1}{2}(\omega'_0 - \omega_0),$$

an angle component ($\delta_1 \cdot \sin \phi_\phi$) of the surface orientation of the wafer along a direction of 90 to 270° may be determined by the following Equation:

$$\delta_1 \cdot \sin \phi_\phi = \frac{1}{2}(\omega'_{\phi 0} - \omega_{\phi 0}), \text{ and}$$

the surface orientation of the single crystal wafer may be measured only by measuring the high-resolution X-ray rocking curve two times at an interval of 90° at each of the two sample orientations of $\Delta\phi_\phi = 180°$.

Advantageous Effects

With the method of determining a surface orientation of a single crystal wafer using high resolution X-ray rocking curve measurement according to an exemplary embodiment of the present invention having the configuration as described above, the direction of the surface angle as well as the surface angle of the wafer is accurately determined, thereby making it possible to contribute to improvement of productivity of the wafer and improve quality of a product. In addition, even in the case in which the rotation axis of the measuring apparatus for measuring the surface orientation of the wafer and the surface normal of the wafer do not coincide with each other, the surface orientation of the wafer may be accurately determined without arranging the rotation axis and the surface normal using a surface orientation standard material. In addition, the misalignment angle formed by the rotation axis of the measuring apparatus and the surface normal and the direction of the misalignment angle may be determined.

BEST MODE

Hereinafter, an exemplary embodiment of the present invention of the present invention will be described in detail with reference to the accompanying drawings.

Theoretical Model

Figure 1:
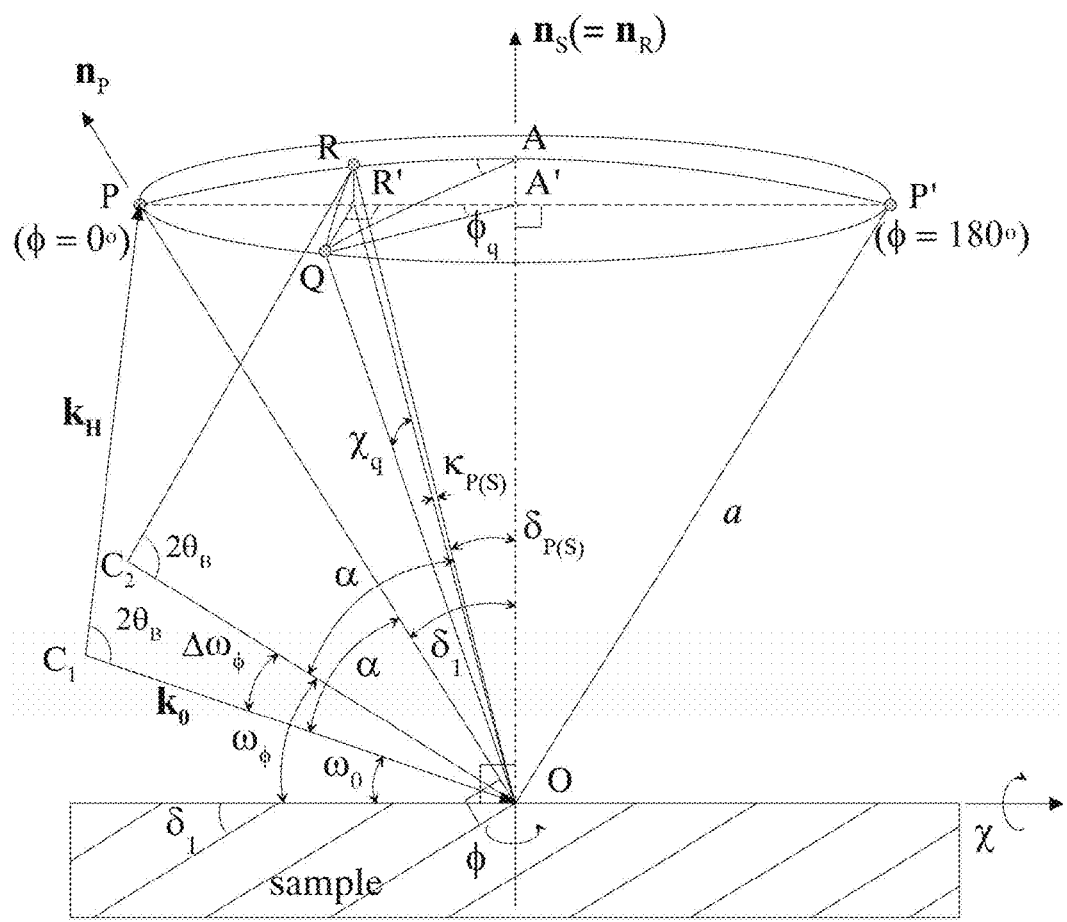
FIG. 1 is a diagram showing a reciprocal lattice space for a single crystal wafer having a crystal plane of a surface orientation angle $\delta_1$ when a surface normal $n_S$ is parallel to a rotation axis $n_R$ of a measuring apparatus.

FIG. 1 shows a reciprocal lattice space for a single crystal wafer having a surface orientation angle $\delta_1$ when a surface normal $n_S$ is parallel to a rotation axis $n_R$ of a measuring apparatus. A reciprocal lattice point for a reflection plane selected in order to measure a rocking curve is shown at a point P along a direction of a crystal plane normal $n_P$.

A diffraction plane containing an incident X-ray beam and a reflected X-ray beam is put in a vertical direction, which is a direction of a paper surface, and passes through an original point O, as shown in FIG. 1. $k_0$ indicates a wave vector of an incident X-ray, and $k_B$ a indicates a wave vector of a reflected X-ray. In FIG. 1, it has been assumed that the crystal plane normal is accurately put on the diffraction plane at $\phi=1$. Therefore, it has been assumed that an optimal Bragg condition is satisfied without any x rotation.

When an incidence angle of an X-ray is $\omega_0$ at an azimuth angle $\phi=0$, the Bragg's law is satisfied for the reciprocal lattice point P. When ignoring refractive index corrections, an incidence angle $\omega_0$ in which a peak of the rocking curve appears is represented by the following Equation.

$$\omega_0 = \frac{\pi}{2} - \alpha - \delta_1 = \theta_B - \delta_1 \quad \text{(Equation 1)}$$

Where $$\alpha = \frac{\pi}{2} - \theta_B,$$

and $\theta_B$ indicates a Bragg angle. When the wafer is rotated with respect to the surface normal $n_R$ by $\phi=\phi_0$, the point P moves to a point Q along a cone having a semi-apex angle of $\delta_1$. The point is, then, rotated along an axis x by $x=x_\phi$ in order to satisfy an accurate Bragg reflection condition and moves to a point R on the diffraction plane. The incident angle $\omega_\phi$ of the lattice point R satisfying the Bragg's law, that is, a peak position of the rocking curve is represented by the following Equation.

$$\omega_\phi = \omega_0 + \Delta\omega_\phi - \delta_{P(S)} = \theta_B - \delta_{P(S)} \quad \text{(Equation 2)}$$

From right triangles $\Delta OA'Q$, $\Delta OA'R'$, and $\Delta A'R'Q$ shown in FIG. 1, the following Equation may be derived.

$$\tan+(\delta_{P(S)}+\kappa_{P(S)})=\tan \delta_1 \cdot \cos \phi_\phi \quad \text{(Equation 3)}$$

In addition, when $\delta_1 > 1$, Equation 3 may be represented by the following Equation.

$$\delta_{P(S)} \cong \delta_1 \cdot \cos \phi_\phi - \kappa_{P(S)} \quad \text{(Equation 4)}$$

Here, Equation 4 may be generalized as the following Equation in consideration of the phase $\phi_\phi$ of the crystal plane normal at which the azimuth angle $\phi$ is rotated by the rotation axis through $\phi-\phi_\phi$.

$$\delta_{P(S)} \cong \delta_1 \cdot \cos(\phi-\phi_\phi) - \kappa_{P(S)} \quad \text{(Equation 5)}$$

$\delta_{P(S)}$ is a function of an angle and indicates an angle between the crystal plane normal and the surface normal on the diffraction plane, and $\kappa_{P(S)}$ varies depending on $\phi$. In addition, from Equations 2 and 5, a variation in the incident angle depending on a variation in the azimuth angle $\phi$ is represented by the following Equation.

$$\omega_\phi \cong \delta_1 \cdot \cos(\phi-\phi_\phi) + \theta_B + \kappa_{P(S)} \quad \text{(Equation 6)}$$

Figure 2:
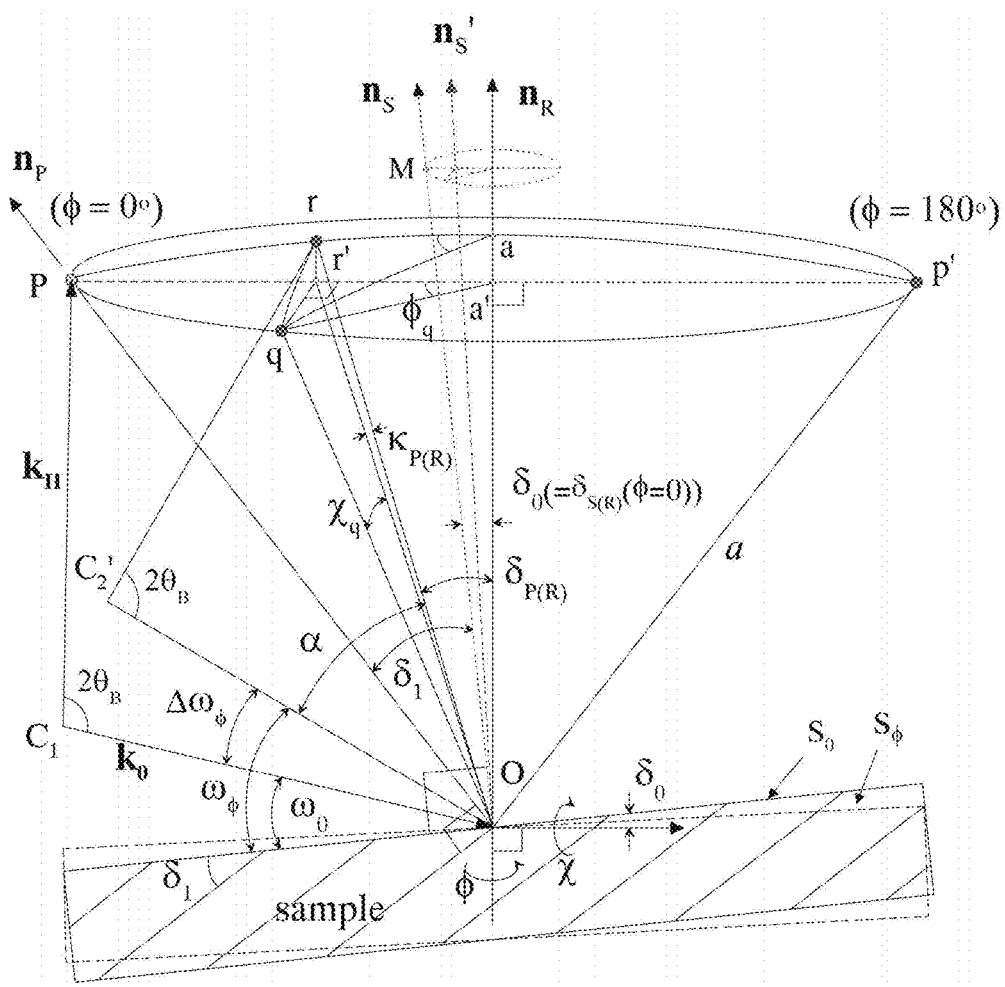
FIG. 2 is a diagram showing a reciprocal lattice space for a single crystal wafer having a crystal plane of a surface orientation angle $\delta_1$ when the surface normal $n_S$ is tilted with respect to the rotation axis $n_R$ of the measuring apparatus by a tilt angle $\delta_0$.

In the case in which the surface normal of the sample is not parallel to the rotation axis of the measuring apparatus, a situation becomes more complicated. FIG. 2 shows a reciprocal lattice space for a single crystal wafer having a crystal plane of a surface miscut $\delta_1$ when the surface normal $n_S$ is not parallel to the rotation axis $n_R$ of the measuring apparatus.

$\delta_0$ indicates a misalignment angle of the surface normal $n_S$ with respect to the rotation axis $n_R$. In FIG. 2, it has been assumed that the crystal plane normal and the surface normal are accurately put on the plane of diffraction at $\phi=0$. Therefore, it has been assumed that an optimal Bragg condition is satisfied without any x rotation.

Referring to FIG. 2, when the reciprocal lattice point P is rotated by $\phi=\phi_\phi$, the reciprocal lattice point P moves to a point $\delta$. The point then moves to a point r on the diffraction plane through $x=x_q$ rotation. At the same time, the surface normal $n_S$ also rotates by $\phi=\phi_\phi$ and $x=x_\phi$. In this case, since $\delta_1=\delta_0$, the surface normal is not present on the diffraction plane. $n_S'$ in FIG. 2 indicates projection of the surface normal $n_S'$ on the diffraction plane after the surface normal rotates by $\phi=\phi_\phi$ and $x=x_\phi$. When the surface normal rotates by $\phi=\phi_\phi$ and $x=x_\phi$, respectively, the position of the sample surface varies from $S_0$ to $S_\phi$, as shown in FIG. 2.

In the case in which the Bragg's law is satisfied for the reciprocal lattice point P at the azimuth angle $\phi=_0$, the incidence angle $\omega_0$ is given as $\omega_0=\theta_B-\delta_1$. As shown in FIG. 2, the incident angle $\omega_\phi$, that is, the peak position of the rocking curve is defined by the following Equation by a Bragg condition for the lattice point r by and x rotation.

$$\omega_\phi = \omega_\phi + \Delta\omega_\phi = \theta_B + \delta_0 - \delta_{P(R)} \quad \text{(Equation 7)}$$

Where $\delta\omega_\phi = \delta_1 + \delta_0 - \delta_{P(R)}$. By analogy with Equation 5, the tilt angle between the surface normal and the rotation axis on the diffraction plane may be represented as a function of $\phi$ by the following Equation.

$$\delta_{S(R)} \cong \delta_0 \cdot \cos(\phi-\phi_\phi) - \kappa_{S(R)} \quad \text{(Equation 7-1)}$$

Where $\phi_\phi$ is a phase for the movement as in Equation 5. $\delta_0$ in Equation 7 indicates the tilt angle of the surface normal from the rotation axis at $\phi=0$ under the condition in shown in FIG. 2.

When using Equation 7-1, the tilt of the surface normal at $\phi=0$ is generalized as $\delta_{S(R)(\phi=0)}=\delta_0 \cdot \cos(-\phi_\phi)\kappa_{S(R)(\phi=0)}$. Therefore, Equation 7 may be represented by the following Equation.

$$\omega_\phi \cong \theta_B + \delta_0 \cdot \cos(-\phi_\phi) - \kappa_{S(R)(\phi=0)} - \delta_{P(R)} \quad \text{(Equation 8)}$$

From right triangles $\Delta O\alpha'\alpha$, $\Delta\alpha'r'$, and $\Delta\alpha'r'\alpha$ shown in FIG. 2 and the condition as in Equation 3, the following Equation may be derived.

$$\tan(\delta_{P(R)}+\kappa_{P(R)})=\tan(\delta_1+\delta_0) \cdot \cos \phi_\phi \quad \text{(Equation 9)}$$

For $\delta_1+\delta_0<1$, Equation 9 may be represented by the following Equation.

$$\delta_{P(R)} \cong \delta_1 \cdot \cos(\phi_\phi + \delta_0 \cdot \cos \phi_\phi - \kappa_{P(R)} \quad \text{(Equation 10)}$$

Equation 10 is also generalized by Equation 5, and each cosine function as in Equation 10 may be represented by the following Equation when considering any phases $\phi_\phi$ and $\phi_\varphi$ defined by Equations 5 and 7-1.

$$\delta_{P(R)} \cong \delta_1 \cdot \cos(\phi - \phi_\phi) + \delta_0 \cdot \cos(\phi - \phi_\varphi) - \kappa_{P(R)} \quad \text{(Equation 11)}$$

$\delta_{P(R)}$ indicates an angle between the crystal plane normal and the rotation axis as a function of $\phi$ on the diffraction plane. In addition, $\kappa_{P(R)}$ varies as the function of $\phi$. $\delta_1 \cdot \cos(\phi - \phi_P)$ indicates a movement component of the crystal plane normal along of a circumference of the surface normal as in Equation 5, $\delta_0 \cdot \cos(\phi - \phi_\varphi)$ and indicates a movement component of the surface normal along a circumference of the rotation axis as in Equation 7-1.

When inserting Equation 11 into Equation 8, the following Equation may be derived.

$$\omega_\phi \cong \delta_1 \cdot \cos(\phi - \phi_\phi) - \delta_0 \cdot \cos(\phi - \phi_\varphi) + \kappa_{P(R)} + \theta_B + \delta_0 \cdot \cos(-\phi_\varphi) - \kappa_{S(R)(\phi=0)} \quad \text{(Equation 12)}$$

Equation 13 may describe a variation of the peak position of the rocking curve for the selected reflection plane as a function of the azimuth angle $\phi$ even though the surface normal is not parallel to the rotation axis. Therefore, when $\delta_0$ is equal to zero, Equation 13 becomes Equation 6.

In Equation 6, when the phase $\phi_\phi$ of the cosine function changes by $\Delta\phi_\phi$, the variation of the incidence angle is represented by the following Equation.

$$\omega'_\phi \cong -\delta_1 \cdot \cos(\phi - \phi_\phi - \Delta\phi_\phi) + \theta_B + \kappa'_{P(S)} \quad \text{(Equation 13)}$$

From Equations 6 and 13, the following Equation may be derived.

$$\omega_\phi - \omega'_\phi = 2\delta_1 \cdot \sin\left(\frac{\Delta\phi_P}{2}\right) \cdot \sin\left(\phi - \phi_P - \frac{\Delta\phi_P}{2}\right) + \kappa_{P(S)} - \kappa'_{P(S)} \quad \text{(Equation 14)}$$

Similar to Equation 12, even though the phase $\phi_\phi$ changes by $\phi_\phi + \Delta\phi_\phi$, the phase $\phi_\varphi$ related to the movement of $\delta_a$ is maintained in a fixed state. Therefore, Equation 12 may be represented by the following Equation.

$$\omega'_\phi \cong -\delta_1 \cdot \cos(\phi - \phi_\phi - \Delta\phi_\phi) - \delta_0 \cdot \cos(\phi - \phi_\varphi) + \kappa'_{P(R)} + \theta_B + \delta_0 \cdot \cos(-\phi_\varphi) - \kappa_{S(R)(\phi=0)} \quad \text{(Equation 15)}$$

From Equations 12 and 15, the following Equation may be derived.

$$\omega_\phi - \omega'_\phi = 2\delta_1 \cdot \sin\left(\frac{\Delta\phi_P}{2}\right) \cdot \sin\left(\phi - \phi_P - \frac{\Delta\phi_P}{2}\right) + \kappa_{P(R)} - \kappa'_{P(R)} \quad \text{(Equation 16)}$$

Figure 3:
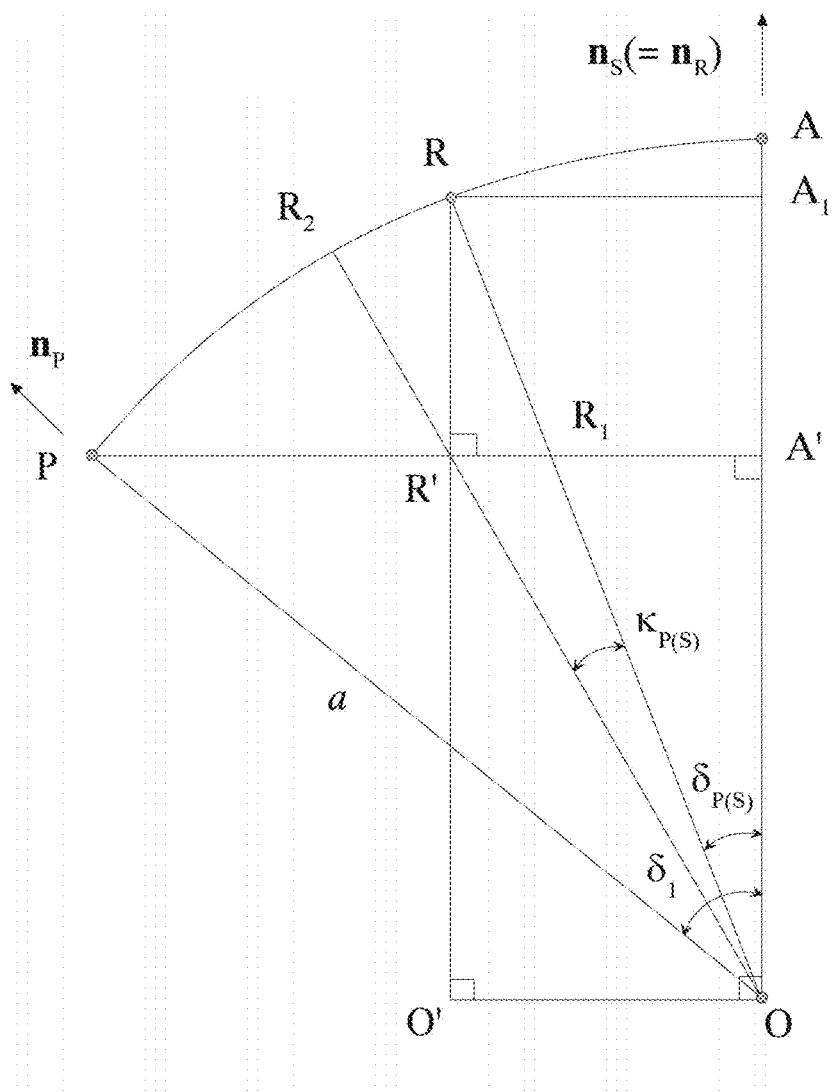
FIG. 3 is a diagram showing a variation of $\kappa_{P(S)}$ on a diffraction plane in the case (See FIG. 1) in which the surface normal is parallel to the rotation axis when a Bragg diffraction condition for a reciprocal lattice point R is satisfied.

FIG. 3 shows a variation of $\kappa_{P(S)}$ on a diffraction plane in the case (See FIG. 1) in which the surface normal is parallel to the rotation axis when a Bragg diffraction condition a reciprocal lattice point 3 is satisfied. As shown in FIG. 3, the following Equation is satisfied from $\Delta OA'R'$.

$$\tan(\delta_{P(S)} + \kappa_{P(S)}) = \frac{\sin\delta_{P(S)}}{\cos\delta_1} \quad \text{(Equation 17)}$$

Therefore, $\kappa_{P(S)}$ may be given as the following Equation.

$$\kappa_{P(S)} = \tan^{-1}\left(\frac{\sin\delta_{P(S)}}{\cos\delta_1}\right) - \delta_{P(S)} \quad \text{(Equation 18)}$$

When inserting Equation 5 into Equation 18, the following Equation may be derived.

$$\kappa_{P(S)} \cong \tan^{-1}\left(\frac{\sin(\delta_1 \cdot \cos(\phi - \phi_P) - \kappa_{P(S)})}{\cos\delta_1}\right) - \delta_1 \cdot \cos(\phi - \phi_P) + \kappa_{P(S)} \quad \text{(Equation 19)}$$

Equation 19 shows the variation of $\kappa_{P(S)}$ as a function of $\phi$ when the surface normal is parallel to the rotation axis.

EXPERIMENTAL EXAMPLE

A surface orientation was measured for a 6 inch (00.1) sapphire wafer used as a substrate for a light emitting diode (LED) and having a nominal surface azimuth angle of 0.2° using the theoretical models described above. A high resolution X-Ray diffractometer (XRD) including a 4-bounce Ge (022) monochromator and a 4-circle goniometer were utilized as the measuring apparatus. In addition, the surface of the wafer was closely attached to a reference surface of a wafer holder. The wafer holder includes a narrow and long slit with different two azimuth angles $\phi_1$ and $\phi_2$ having an angle difference of 120° therebetween. The two slits were configured to be parallel to reference edges of the wafer at $\phi_1$ and $\phi_2$, respectively.

Measurements of rocking curves were carried out as follows. At any one azimuth angle of the sample waver at $\phi=\phi_1$, rocking curves of an optimum Bragg conditions for a sapphire (00.6) crystal plane were measured six times at each of the different azimuths at an interval of 60° (for example, $\phi=0$, 60, 120, 180, 240 및 360). In addition, the peak position of each rocking curve was recorded. After the measurements at $\phi=\phi_1$, the wafer was removed from the holder and the sample was again fixed to the holder so that $\phi=\phi_2$. Then, the rocking curves were measured six times as described above. Before rocking curve measurements, an azimuth angle of the wafer mounted on the holder were accurately determined. The narrow and long slit of the holder parallel to the reference edge of the wafer was aligned to be parallel to a direction of the X-ray through a $\phi$ scan. In this case, the peak position was determined as $\phi=\phi_1$. After rotating the wafer to $\phi=\phi_2$, another slit in the holder was aligned to be parallel to the direction of the X-ray through a $\phi$ scan. In this case, the peak position was determined as $\phi=\phi_2$. A difference of $\Delta\phi_\phi=\phi_2-\phi_1$ becomes a phase change for the surface orientation measurement.

Result

Figure 4:
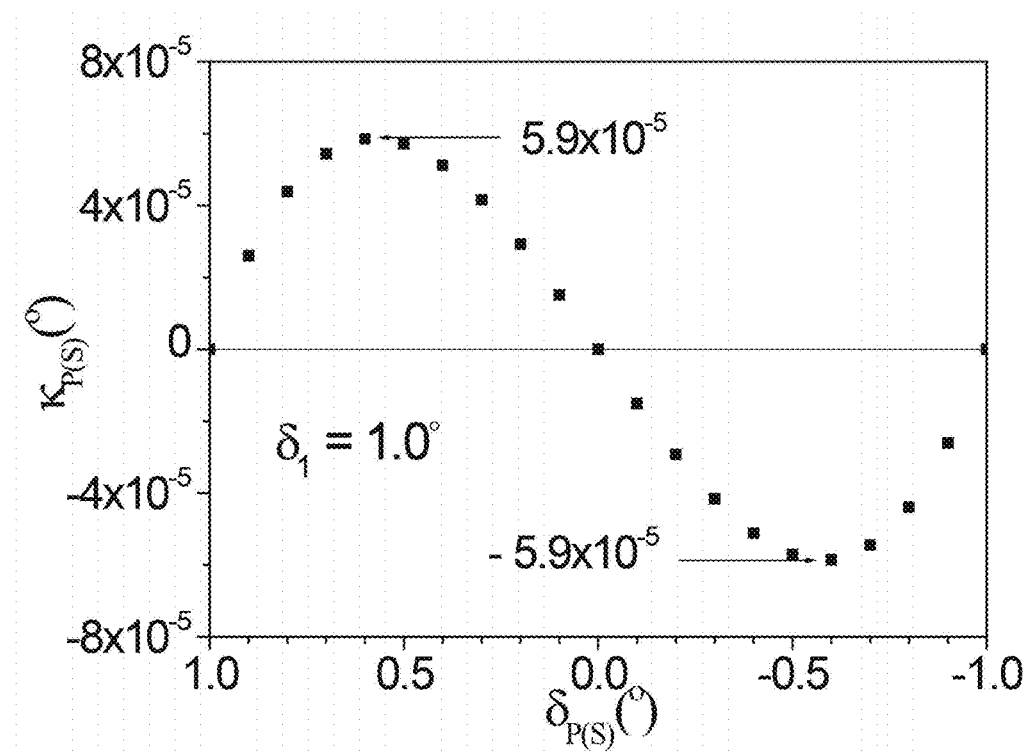
FIG. 4 is a diagram showing a result of a $\kappa_{P(S)}$ value when $\delta_{P(S)}$ changes from $\delta_1$ to $-\delta_1$ for a sample with $\delta_1 = 1.0°$.

Assuming that the phase angle $\phi_\phi=0$, the angle $\delta_{P(S)}$ between the crystal plane normal and the surface normal on the diffraction plane shown in FIG. 1 varies from $\delta_1$ to $-\delta_1$ when the azimuth angle rotates from $\phi$ to $\pi$. $\kappa_{P(S)}$ is calculated according to Equation 19 when $\delta_{P(S)}$ changes from $\delta_1$ to $\delta_1$ for a sample with $\delta_1=1.0°$. The result is shown in FIG. 4. Maximum and minimum values of $\kappa_{P(S)}$ are $\pm 5.9 \times 10^{-6}(°)$ and the values of $\kappa_{P(S)}$ are negligibly small as compared to the surface angle $\delta_1=1.0°$.

Table 1 shows maximum and minimum values of $\kappa_{P(S)}$ calculated according to Equation 18 for samples with $\delta_1=0.2$, 1.0, 1.5, 2.0, 2.5 and 3.0. It could be appreciated that the maximum and minimum values are very small as compared to the surface angles.

TABLE 1

| $\delta_1$ (°) | $\kappa_{P(S)}$ (°) max. (+)/min.(−) | $\kappa_{P(S)} - \kappa'_{P(S)}$ (°) max (+)/min. (−) |
|---|---|---|
| 0.2 | ±4.7 × 10$^{-7}$ | ±4.7 × 10$^{-7}$ |
| 1.0 | ±5.9 × 10$^{-5}$ | ±5.9 × 10$^{-5}$ |
| 1.5 | ±2.0 × 10$^{-4}$ | ±2.0 × 10$^{-4}$ |
| 2.0 | ±4.7 × 10$^{-4}$ | ±4.7 × 10$^{-4}$ |
| 2.5 | ±9.2 × 10$^{-4}$ | ±9.2 × 10$^{-4}$ |
| 3.0 | ±1.6 × 10$^{-3}$ | ±1.6 × 10$^{-3}$ |

Therefore, since $\kappa_{P(S)}$ is extremely smaller than $\delta_1$, $\kappa_{P(S)}$ at the right side of Equation 19 can be neglected. Therefore, Equation 19 may be represented by the following Equation.

$$\kappa_{P(S)} \cong \tan^{-1}\left(\frac{\sin(\delta_1 \cdot \cos(\phi - \phi_P))}{\cos\delta_1}\right) - \delta_1 \cdot \cos(\phi - \phi_P) \quad \text{(Equation 20)}$$

Figure 5:
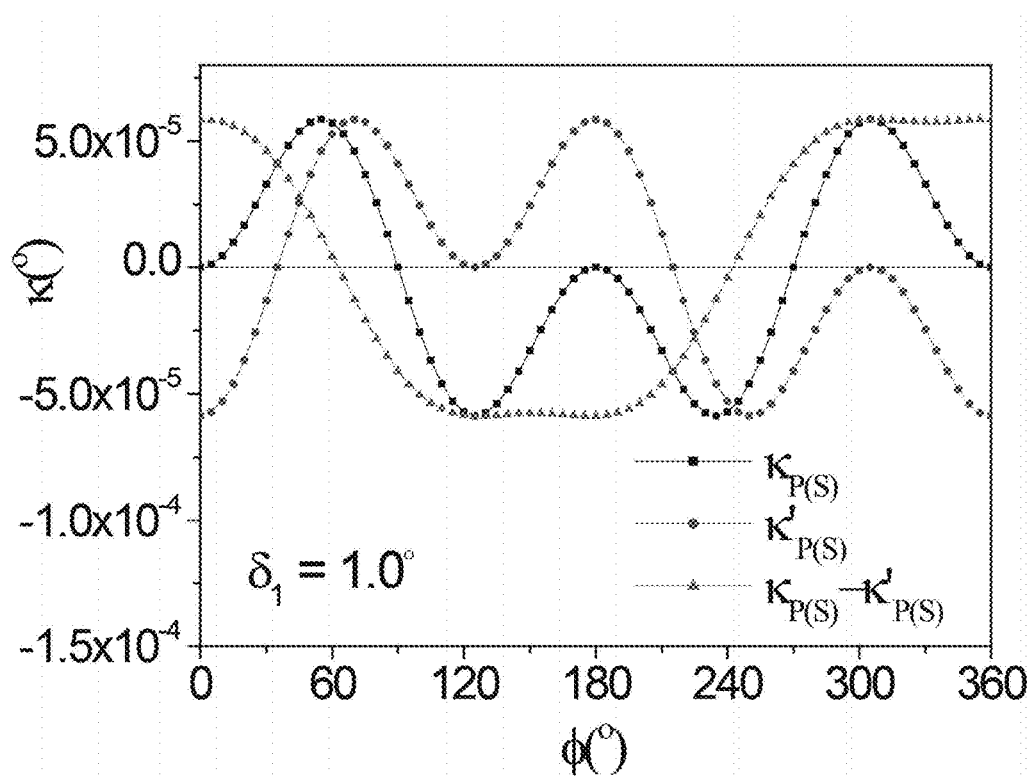
FIG. 5 is a diagram showing a result of a $\kappa_{P(S)}$ value calculated as a function of an azimuth angle for $\delta_1 = 1.0°$ when it is assumed that a phase angle $\phi_\phi = 0$.

When assuming a phase $\phi_\phi = 0$, $\kappa_{P(S)}$ is calculated as a function of the azimuth angle for $\delta_1 = 1.0°$ according to Equation 20. The result is shown in FIG. 5. The variation is symmetric around $\phi = 180°$, and the value of $\kappa_{P(S)}$ is 0 when $\phi = 0, 90, 180$ and 270 as shown in FIG. 1. When a phase of a cosine function in Equation 20 shifts by $\Delta\phi_\phi$, a difference $\kappa_{P(S)} - \kappa'_{P(S)}$ between two values in Equation 14 for the wafer having $\delta_1 = 1.0°$ has the smallest maximum value of $5.9 \times 10^{-6}$(°) when $\Delta\phi_\phi = 125°$. The value in this case is equal to the maximum value of $\kappa_{P(S)}$. The variations of $\kappa'_{P(S)}$ and $\kappa_{P(S)} - \kappa'_{P(S)}$, which are a function of the azimuth angle $\phi$ for the phase change of $\Delta\phi_\phi = 125°$, are shown in FIG. 5 together with the variation of $\kappa_{P(S)}$. The maximum and minimum values in $\kappa_{P(S)} - \kappa'_{P(S)}$ values when $\Delta\phi_\phi = 125°$ for different $\delta_1$ values are also shown in Table 1 together with those in the respective $\kappa_{P(S)}$ values. In this experiment, a phase shift of $\Delta\phi_\phi = 125°$ was employed at the time of designing the wafer holder and the difference $\kappa_{P(S)} - \kappa'_{P(S)}$ for the phase change when $\Delta\phi_\phi = 125°$ was neglected during analysis.

As described above, the rocking curves under the optimum Bragg conditions for the sapphire (00.6) crystal plane were measured six times at a sample azimuth angle $\phi = \phi_1$ and were additionally measured six times at a sample azimuth angle $\phi = \phi_2$. Table 2 shows the peak positions of the rocking curves at each azimuth In addition, the measured phase change $\Delta\phi_\phi = \phi_2 - \phi_1$ was 120.19°.

TABLE 2

$\delta_{P(S)}$ = OCA, $\delta_{S(R)} = \delta_0 \cdot \cos(\phi - \phi_s)$ ($\Delta\phi_p = 120.19$)

| $\phi$ (°) | $\omega_\phi$ | $\omega'_\phi$ | $\omega_\phi - \omega'_\phi$ | $\delta_{P(S)}$ | $\omega_\phi + \delta_{P(S)}$ |
|---|---|---|---|---|---|
| 0 | 20.6318 | 20.9591 | −0.3273 | 0.1979 | 20.8297 |
| 60 | 20.6797 | 20.7389 | −0.0592 | 0.1279 | 20.8076 |
| 90 | 20.7664 | | | | |
| 120 | 20.8680 | 20.5985 | 0.2695 | −0.0700 | 20.7980 |
| 180 | 21.0074 | 20.6816 | 0.3258 | −0.1979 | 20.8095 |
| 240 | 20.9587 | 20.9013 | 0.0574 | −0.1279 | 20.8308 |
| 270 | 20.8744 | | | | |
| 300 | 20.7753 | 21.0408 | −0.2655 | 0.0700 | 20.8453 |

Since the rotation axis of a goniometer is not usually parallel to the surface normal of the sample, Equation 16 was used toe analyze the surface orientation. From $\omega_\phi$ and $\omega'_\phi$ in Table 2, $\omega_\phi - \omega'_\phi$ is calculated at each $\phi$. This is also shown in Table 2. $\omega_\phi - \omega'_\phi$ at each may be fitted to a sine function using the least squares method according to Equation 16. The term $\kappa_{P(R)} - \kappa'_{P(R)}$ may be neglected. The reason is that the value is negligibly small in the case in which $\delta_1 \approx 0.2°$, as shown in Table 1. Therefore, $\omega_\phi - \omega'_\phi$ is determined by the following Equation.

$$\omega_\phi - \omega'_\phi \cong 2\delta_1 \cdot \sin\frac{\Delta\phi_P}{2} \cdot \sin\left(\phi - \phi_P - \frac{\Delta\phi_P}{2}\right) = \quad \text{(Equation 21)}$$
$$0.348 \cdot \sin(\phi - 69.69) + 0.0001$$

Figure 6:
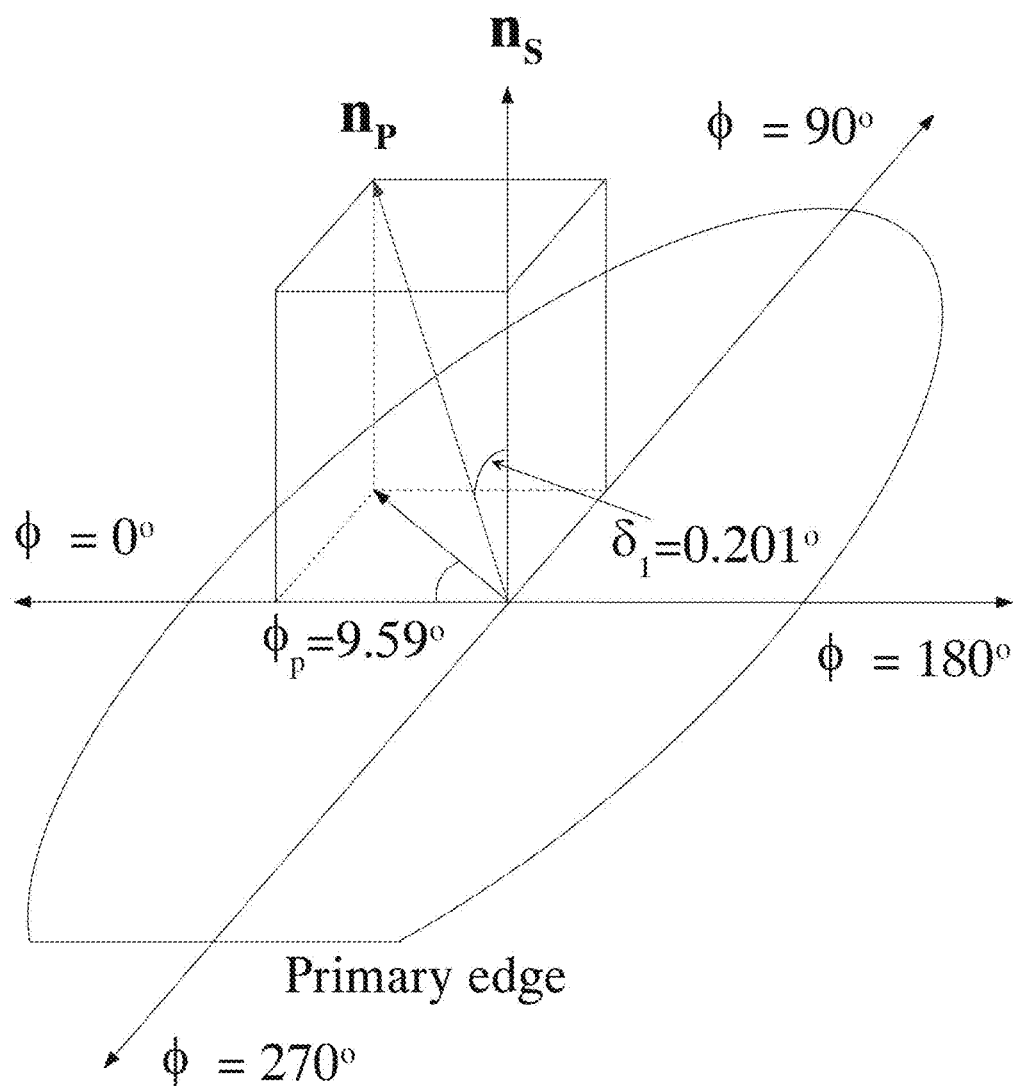
FIG. 6 is a diagram showing a sample wafer having a miscut of $\delta_1=0.201°$ and $\phi_\phi=9.59°$ from a reference edge.

According to Equation 21, $\delta_1 = 0.201°$ and $\phi_\phi = 9.59°$ may be obtained using $\Delta\phi_\phi = 120.19°$. Therefore, the sample wafer has a surface miscut of $\delta_1 = 0.201°$ at $\phi_\phi = 9.59°$ from the reference edge of the sample. The result is schematically shown in FIG. 6. From Equation 5, the variation $\delta_{P(S)}$ of the surface orientation of the wafer as the function of $\phi$ may be defined by the following Equation.

$$\delta_{P(S)} \cong 0.201 \cdot \cos(\phi - 9.59) \quad \text{(Equation 22)}$$

Figure 7:
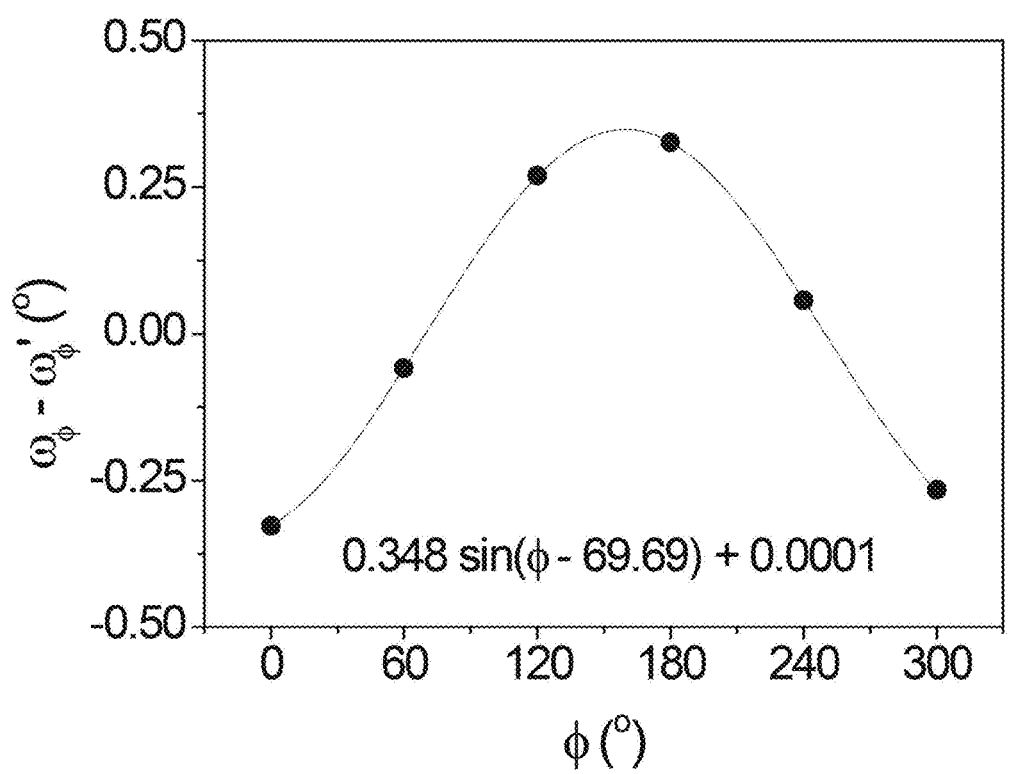
FIG. 7 is a diagram showing the least-square-fit of $\omega_\phi-\omega'_\phi$ by a sine function.

The least squares fit in Equation 21 for $\omega_\phi - \omega'_\phi$ by a sine function is shown in FIG. 7. The value of $x^2$ for the fitting is $3.7 \times 10^{-6}$ corresponding to an extremely small value, which shows that the confidence level of the fit is very high.

Using Equation 5, Equation 12 may be rewritten as the following Equation.

$$\omega_\phi + \delta_{P(S)} \cong -\delta_0 \cdot \cos(\phi - \phi_\phi) + \theta_B + \delta_0 \cdot \cos(-\phi_\phi) - \kappa_{S(R)(\phi=0)} + \kappa_{P(R)} - \kappa_{P(S)} \quad \text{(Equation 23)}$$

$\delta_{P(S)}$ and $\omega_\phi + \delta_{P(S)}$ at each $\phi$ are calculated together with the measurement values of the peak positions $\omega_\phi$ and $\omega'_\phi$ as shown in Table 2. According to Equation 23, the value of $\omega_\phi + \delta_{P(S)}$ is fitted to a cosine function as a function of $\phi$ using the least squares method. The result is represented by the following Equation.

$$\omega_\phi + \delta_{P(S)} \cong -0.023 \cdot \cos(\phi - 297.85) + 20.820 \quad \text{(Equation 24)}$$

Therefore, the variation $\delta_{S(R)}$ of the tilt of the surface normal from the rotation axis as a function of $\phi$ is determined as represented by the following Equation.

$$\delta_{S(R)} \cong 0.023 \cdot \cos(\phi - 117.85) \quad \text{(Equation 25)}$$

Where when neglecting the term $-\kappa_{S(R)(\phi=0)} + \kappa_{P(R)} - \kappa_{P(S)}$ in Equation 23, Equation 25 shows that the maximum misalignment $\delta_0 = 0.023°$ at $\phi_\phi = 117.85°$.

Horizontal and vertical components of the surface orientation of the sample wafer were measured according to the ASTM standard (ASTM F26-87a, Standard Test Method for Determining the Orientation of a Semiconductive Single Crystal) and were compared to the results of the present experiment. When neglecting $\kappa_{P(R)}$, at $\delta_1$ and $\delta_0$, Equation 12 may be defined by the following Equations, respectively.

$$\omega_0 \cong -\delta_{P(S)(\phi=0)} - \delta_{S(R)(\phi=0)} + \theta_B + \delta_0 \cdot \cos(-\phi_S) - \kappa_{S(R)(\phi=0)} \quad \text{(Equation 26)}$$

$$\omega_{180} \cong -\delta_{P(S)(\phi=180)} - \delta_{S(R)(\phi=180)} \theta_B + \delta_0 \cdot \cos(-\phi_S) - \kappa_{S(R)(\phi=0)} \quad \text{(Equation 27)}$$

From Equations 26 and 27, the following Equation may be derived.

$$\frac{\omega_{180} - \omega_0}{2} = \quad \text{(Equation 28)}$$
$$-\frac{\delta_{P(S)(\phi=180)} - \delta_{P(S)(\phi=0)}}{2} - \frac{\delta_{S(R)(\phi=180)} - \delta_{S(R)(\phi=0)}}{2}$$

Where the value $$\frac{(\omega_{180} - \omega_0)}{2}$$

by the ASTM may be obtained from at $\omega_\phi$ at $\phi=0°$ and $180°$ in Table 2, and Equation 28 may be defined by the following Equation.

$$\frac{\Delta\omega}{2} + \frac{\Delta\delta_{S(R)}}{2} = -\frac{\Delta\delta_{P(S)}}{2} \quad \text{(Equation 29)}$$

Table 3 shows comparison results between the ASTM method and the present experiment and the relation between the two values that may be obtained according to Equation 29. The vertical component along a direction of 90°~270° by the ASTM method is obtained from $\omega_\phi$ at $\phi=90°$ and $270°$ in Table 2. Since the ASTM method does not incorporate the misalignment $\delta_{S(R)}$ of the surface normal from the rotation axis, $\Delta\omega/2$ and $-\Delta\delta_{P(S)}/2$ are not consistent with each other. However, when $\delta_{S(R)}$ is incorporated in $\Delta\omega/2$, $\Delta\omega/2+\Delta\delta_{S(R)}/2$ and $-\Delta\delta_{P(S)}/2$ are almost equal to each other within measurement errors.

TABLE 3

| Surface orientation(°) | $-\Delta\delta_{P(S)}/2$ | $\Delta\omega/2$ | $\Delta\delta_{S(R)}/2$ | $(\Delta\delta_{S(R)} + \Delta\omega)/2$ |
|---|---|---|---|---|
| Horizontal(0-180) | 0.198 | 0.188 | 0.011 | 0.199 |
| Vertical(90-270) | 0.033 | 0.054 | −0.020 | 0.034 |

In the present experiment, the rocking curves were measured six times per 60° at two different sample azimuth angles, that is, were measured twelve times, in order to increase precision of the fitting. However, it is sufficient in obtaining the surface orientation and the misalignment of the surface normal to measure the rocking curves four times per 90° at two different sample azimuth angles, that is, to measure the rocking curves eight times. In addition, in the present experiment, when the number of measurements of the rocking curves is increased, the precision of the analysis may be further increased.

As described in Equation 25, the surface normal of the sample used in the present experiment has a maximum misalignment angle, that is, tilt angle $\delta_0=0.023°$ at $\phi_\phi=117.85°$ from the rotation axis defined in the goniometer. In order to adjust the misalignment angle between the surface normal and the rotation axis of the goniometer, the misalignment angle was carefully adjusted by $-0.023°$ at $\phi=117.85°$ to make the surface normal $\delta_0=0°$ of the sample. Then, the measurement was again performed.

Table 4 shows results of the measurement values, and the variation of the surface orientation of the sample as a function of $\phi$ is represented by the following Equation.

$$\delta_{P(S)} \cong 0.201 \cdot \cos(\phi - 10.06) \quad \text{(Equation 30)}$$

TABLE 4

| $\phi$ (°) | $\omega_\phi$ | $\omega'_\phi$ | $\omega_\phi - \omega'_\phi$ | $\delta_{P(S)}$ | $\omega_\phi + \delta_{P(S)}$ |
|---|---|---|---|---|---|
| \multicolumn{6}{c}{$\delta_{P(S)}$ = OCA, $\delta_{S(R)}$ = $\delta_0 \cdot \cos(\phi - \phi_s)$ ($\Delta\phi_p$ = 120.06)} |
| 0 | 20.6327 | 20.9610 | −0.3283 | 0.1980 | 20.8307 |
| 60 | 20.6961 | 20.7576 | −0.0615 | 0.1294 | 20.8255 |
| 120 | 20.8917 | 20.6241 | 0.2676 | −0.0686 | 20.8231 |
| 180 | 21.0247 | 20.6977 | 0.3270 | −0.1980 | 20.8267 |

TABLE 4-continued

| $\phi$ (°) | $\omega_\phi$ | $\omega'_\phi$ | $\omega_\phi - \omega'_\phi$ | $\delta_{P(S)}$ | $\omega_\phi + \delta_{P(S)}$ |
|---|---|---|---|---|---|
| \multicolumn{6}{c}{$\delta_{P(S)}$ = OCA, $\delta_{S(R)}$ = $\delta_0 \cdot \cos(\phi - \phi_s)$ ($\Delta\phi_p$ = 120.06)} |
| 240 | 20.9612 | 20.9008 | 0.0604 | −0.1294 | 20.8318 |
| 300 | 20.7679 | 20.0332 | −0.2653 | 0.0686 | 20.8365 |

Equation 30 is almost the same as the result in Equation 22. The variation, that is, the misalignment, of the tilt of the surface normal from the rotation axis, is represented by the following Equation.

$$\delta_{S(R)} \cong 0.006 \cdot \cos(\phi - 114.03) \quad \text{(Equation 31)}$$

The adjusted maximum tilt of the surface normal is $\delta_0=0.006°$, and the tilt is very small as compared to an original value $\delta_0=0.023°$ before the adjustment.

The value $\theta_B + \delta_0 \cdot \cos(-\phi_S) - \kappa_{S(R)(\phi=0)}$ in Equation 23 may be obtained from the measurement results in Table 2 and 4 are equal to 20.820° and 20.829° when neglecting $\kappa_{S(R)(\phi=0)}$. Bragg angles for the used diffraction plane are 20.831° and 20.832°. The two Bragg angles are almost the same as each other within experimental errors and are comparable to the theoretical value of 20.838° for a crystal plane (00.6) of sapphire.

L. D. Doucette (L. D. Doucette et al, Review of Scientific Instruments 76, 036106, 2005) measured surface orientations for several single crystal wafers having miscuts of 5° or less by measuring rocking curves four times per 90° as a function of an azimuth angle at each of the two different sample azimuths ($\Delta\phi_\phi=180°$), that is, by measuring the rocking curves eight times. They considered the tilt angle $\delta_{S(R)}$ of the surface normal by Equation 7-1 in the present experiment with respect to the rotation axis.

When neglecting $\kappa_{P(R)}$ and $\kappa'_{P(R)}$ and using Equations. 12 and 15, a horizontal component of the surface orientation along a direction of 0 to 180° is obtained. The horizontal component has the following relationship with Equation 4 of L. D. Doucette.

$$\delta_1 \cdot \cos\phi_P = \frac{1}{4}\{(\omega_{180} - \omega_0) - (\omega'_{180} - \omega'_0)\} = \quad \text{(Equation 32)}$$

$$-\frac{1}{4}\{(\omega'_1 - \omega'_2) + (\omega'_{2t} - \omega'_{1t})\}$$

Where the sign relations are different, but the two results are equivalent to each other.

In the case of a wafer of a very small surface miscut, in order to calculate the horizontal component $\delta_1 \cdot \cos \phi_\phi$ of the surface orientation along the direction of 0 to 180°, it is sufficient to measure the rocking curves only time times at two sample azimuths of $\Delta\phi_\phi=180°$. Therefore, when neglecting $\kappa_{P(R)}$ and $\kappa'_{P(R)}$ and using Equations. 12 and 15, an angular component along 0 to 180° is represented by the following Equation.

$$\delta_1 \cdot \cos \phi_\phi = \frac{1}{2}(\omega'_0 - \omega_0) \quad \text{(Equation 33)}$$

Similarly, an angular component along 90 to 270° is represented by the following Equation.

$$\delta_1 \cdot \sin \phi_\phi = \frac{1}{2}(\omega'_{90} - \omega_{90}) \quad \text{(Equation 34)}$$

Therefore, the rocking curves are measured only two times at an interval of 90° at each of two sample azimuths of $\Delta\phi_\phi=180°$, that is, are measured only four times, thereby making it possible to calculate the surface orientation of the single crystal wafer.

CONCLUSION

According to the exemplary embodiment of the present invention, theoretical models to completely describe the variation of the peak positions of the rocking curve as the function of the azimuth angle in both of the cases that the surface normal of the wafer is parallel and is not parallel to the rotation axis of the goniometer have been proposed. Based on these models, an accurate measurement method for the surface orientation of a single crystal wafer having a small surface miscut less than 3° has been proposed through rocking curve measurements using a high-resolution XRD. According to the exemplary embodiment of the present invention, it is possible to calculate the misalignment angle of the surface normal of the same with respect to the rotation axis of the goniometer as well as the surface orientation of the wafer. The surface orientation has been measured for a 6 inch sapphire wafer used for an LED substrate in the present invention. The surface orientation was measured to be $\delta_1 = 0.201°$ at $\phi = 9.59°$ from the reference edge of the wafer in a clockwise direction. In addition, the misalignment of the surface normal from the rotation axis was measured to be $\delta_0 = 0.023°$ at $\phi = 117.85$, and was re-adjusted to 0.006°. During the analysis, geometrical angle components $\kappa_{P(S)}$ and $\kappa_{P(S)} - \kappa'_{P(S)}$ were calculated as the function of the azimuth angle and were negligibly small for the wafer having the surface miscut less than 3°. Surface orientations determined by the ASTM method were compared to the result values obtained by the present invention. The two results were consistent with each other when considering the tilt angle, that is, the misalignment, formed by the rotation axis and the surface normal. Finally, a method capable of simply and accurately calculating the surface orientation of the wafer by measuring the rocking curves two times at an interval of 90° at each of the two sample azimuths having a difference of 180°, that is, by measuring the rocking curves four times has been proposed.

The present invention should not be construed to being limited to the above-mentioned exemplary embodiment. The present invention may be applied to various fields and may be variously modified by those skilled in the art without departing from the scope of the present invention claimed in the claims. Therefore, it is obvious to those skilled in the art that these alterations and modifications fall in the scope of the present invention.

The invention claimed is:

1. A method of measuring a surface orientation of a single crystal wafer in order to determine the surface orientation formed by a crystal plane normal of a single crystal and a surface normal of the wafer, comprising:

measuring a high-resolution X-ray rocking curve of a selected diffraction plane under a Bragg diffraction condition by rotating the wafer by a predetermined azimuth angle ($\phi$) with respect to a rotation axis of an apparatus for measuring the surface orientation, determining a position ($\omega_\phi$) of a maximum peak of the high-resolution X-ray rocking curve by the following Equation:

$$\omega_\phi \cong -\delta_1 \cdot \cos(\phi - \phi_\phi) - \delta_0 \cdot \cos(\phi - \phi_\psi) + \kappa_{P(R)} + \theta_B + \delta_0 \cdot \cos(-\phi_\psi) - \kappa_{S(R)(\phi=0)},$$

where $\delta_1$ indicates an angle (surface angle) of the crystal plane normal with respect to the surface normal, $\phi_\phi$ indicates a direction in which the surface angle appears, $\delta_0$ indicates a misalignment angle formed by the rotation axis of the apparatus for measuring the surface orientation and the surface normal, $\phi_\psi$ indicates a direction of a misalignment axis, $\kappa_{P(R)}$ indicates a small angle component which appears as the crystal plane normal is projected on the diffraction plane at the azimuth angle ($\phi$) in the case in which the surface normal is not parallel to the rotation axis of the apparatus for measuring the surface orientation, $\theta_B$ indicates a Bragg angle, and $\kappa_{S(R)}$ indicates a small angle component which appears as the surface normal is projected on the diffraction plane at the azimuth angle ($\phi$) in the case in which the surface normal is not parallel to the rotation axis of the apparatus for measuring the surface orientation, wherein the surface angle ($\delta_1$) of the wafer and the direction ($\phi_\phi$) in which the surface angle appears is determined by the following Equation:

$$\omega_\phi - \omega'_\phi \cong 2\delta_1 \cdot \sin\frac{\Delta\phi_P}{2} \cdot \sin\left(\phi - \phi_P - \frac{\Delta\phi_P}{2}\right),$$

where $\Delta\phi_\phi$ indicates a phase change value applied at a time of designing a wafer holder, and $\omega_\phi - \omega'_\phi$ indicates an angle difference between peaks of the high-resolution X-ray rocking curve each measured depending on $\Delta\phi_\phi$, and determining a variation ($\delta_{P(S)}$) of the surface orientation of the wafer depending on a function of the azimuth angle ($\phi$) by the following Equation:

$$\delta_{P(S)} \cong \delta_1 \cdot \cos(\phi - \phi_\phi),$$

wherein the high-resolution X-ray rocking curve is measured two times at $\phi = \phi_1$ and $\phi = \phi_2$, and $\Delta\phi_\phi$ is determined by the following Equation:

$$\Delta\phi_\phi = \phi_2 - \phi_1,$$

wherein an angle component ($\delta_1 \cdot \cos \phi_\phi$) of the surface orientation of the wafer along a direction of 0 to 180° is determined by the following Equation:

$$\delta_1 \cdot \cos \phi_\phi = \frac{1}{2}(\omega'_0 - \omega_0),$$

wherein an angle component ($\delta_1 \cdot \sin \phi_\phi$) of the surface orientation of the wafer along a direction of 90 to 270° is determined by the following Equation:

$$\delta_1 \cdot \sin \phi_\phi = \frac{1}{2}(\omega'_{90} - \omega_{90}), \text{ and}$$

wherein the surface orientation of the single crystal wafer is measured only by measuring the high-resolution X-ray rocking curve two times at an interval of 90° at each of two sample azimuth angles of $\Delta\phi_\phi = 180°$.

2. The method of claim 1, wherein a tilt angle ($\delta_{S(R)}$) of the surface normal of the wafer is determined by the following Equation:

$$\delta_1 \cdot \cos \phi_\phi = \frac{1}{2}(\omega'_0 - \omega_0),$$

where $\phi_\phi$ indicates a phase of the surface normal, and $\kappa_{S(R)}$ indicates a small angle component which appears as the surface normal is projected on the diffraction plane at the azimuth angle ($\phi$) in the case in which the surface normal is not parallel to the rotation axis of the apparatus for measuring the surface orientation.

3. The method of claim 1, wherein at a rotation angle $\phi = 0$, the position ($\omega_\phi$) of the maximum peak of the high-resolution X-ray rocking curve is determined by the following Equation:

$$\omega_\phi \cong \theta_B + \delta_0 \cdot \cos(-\phi_\psi) - \kappa_{S(R)(\phi=0)} - \delta_{P(R)}$$

where $\phi_\phi$ indicates a phase of the surface normal, and $\kappa_{S(R)}$ indicates a small angle component which appears as the surface normal is projected on the diffraction plane at the azimuth angle ($\phi$) in the case in which the surface normal is not parallel to the rotation axis of the apparatus for measuring the surface orientation.

4. The method of claim 1, wherein an angle ($\delta_{P(R)}$) between the rotation axis and the crystal plane normal having a function of $\phi$ on the diffraction plane is determined by the following Equation:

$$\delta_{P(R)} \cong \delta_1 \cdot \cos(\phi-\phi_\psi) + \delta_0 \cdot \cos(\phi-\phi_\phi) - \kappa_{P(R)}$$

where $\delta_1 \cdot \cos(\phi-\phi_\psi)$ indicates an angle component of the crystal plane normal changed along a circumference of the surface normal, and $\delta_0 \cdot \cos(\phi-\phi_\phi)$ indicates an angle component of the surface normal changed along a circumference of the rotation axis.

5. The method of claim 1, wherein a tilt variation ($\theta_{S(R)}$) of the surface normal from the rotation axis depending on a function of an orientation angle ($\phi$) is determined by the following Equation:

$$\delta_{S(R)} \cong \delta_0 \cdot \cos(\phi-\phi_\phi)$$

where $\delta_0$ indicates the misalignment angle formed by the rotation axis and the surface normal, and $\phi_\phi$ indicates the direction of the misalignment axis.

* * * * *